United States Patent [19]

Katz

[11] Patent Number: 4,627,842
[45] Date of Patent: Dec. 9, 1986

[54] INTRAVENOUS NEEDLE ASSEMBLY

[76] Inventor: William Katz, 548 Gypsy La., Youngstown, Ohio 44505

[21] Appl. No.: 672,926

[22] Filed: Nov. 19, 1984

[51] Int. Cl.$^4$ ............................................. A61M 5/32
[52] U.S. Cl. ........................... 604/177; 128/DIG. 26; 604/180
[58] Field of Search ............... 604/161, 164, 165, 169, 604/174, 177, 179, 272; 128/133, DIG. 26, 340, DIG. 6

[56] References Cited

U.S. PATENT DOCUMENTS

| 2,402,306 | 6/1946 | Turkel | 128/DIG. 26 |
| 2,409,432 | 10/1946 | Hubbard | 604/179 |
| 2,525,398 | 10/1950 | Collins | 604/179 |
| 3,064,648 | 11/1962 | Bujan | 604/177 |
| 3,461,869 | 8/1969 | Hargest | 128/DIG. 26 |
| 4,250,880 | 2/1981 | Gordon | 604/180 |
| 4,316,461 | 2/1982 | Marais et al. | 604/179 |
| 4,380,234 | 4/1983 | Kamen | 604/180 |
| 4,392,856 | 7/1983 | Lichtenstein | 604/177 |
| 4,397,641 | 8/1983 | Jacobs | 128/DIG. 26 |
| 4,516,293 | 5/1985 | Beran | 128/DIG. 26 |
| 4,563,177 | 1/1986 | Kamen | 604/177 |
| 4,565,544 | 1/1986 | Müller et al. | 604/164 |

Primary Examiner—C. Fred Rosenbaum
Assistant Examiner—Jerome R. Smith, Jr.
Attorney, Agent, or Firm—Harpman & Harpman

[57] ABSTRACT

An intravenous needle assembly includes a hollow needle having a beveled point, the needle being positioned transversely of a central section of an elongated, flexible, foldable body having oppositely disposed wing sections. The needle is provided with a flexible connecting tube and a connector for attachment to a desired device, such as a syringe, bottle, etc. The central section mounting the needle and the oppositely disposed wing sections carry a tapered foam pad with a pressure sensitive adhesive on the lower surface thereof when applied to the skin of a patient's body. After the insertion of the needle in a vein, the needle is angled downwardly into the vein to position the beveled pointed end away from the walls of the vein.

4 Claims, 4 Drawing Figures

INTRAVENOUS NEEDLE ASSEMBLY

BACKGROUND OF THE INVENTION

1. Technical Field

This invention relates to intravenous needle assemblies such as employed in infusion sets.

2. Description of the Prior Art

Prior devices of this type may be seen in U.S. Pat. Nos. 2,670,735, 2,725,058, 3,064,648, 3,863,631, 4,324,236 and 4,392,856.

The needle of Patent 2,670,735 is carried in an elongated tubular member which in turn is provided with sidewardly extending skin grasping members formed of metal. There is no similar construction in the present disclosure.

U.S. Pat. No. 2,725,058 positions the needle transversely of a pair of extending wings and beneath a vertical projection 10 which provides a hand hold for inserting the needle.

In the present invention, oppositely disposed wings sections of a body through which the needle is positioned are foldable upwardly to form a portion by which the needle may be grasped and subsequently folded downwardly to secure the needle to a patient's skin. More importantly, the present invention utilizes a tapered foam pad on the lower portion of the needle carrying device so that the angle of inclination of the needle when positioned through a patient's skin and into a vein is such that the beveled pointed end of the hollow needle is spaced with respect to the walls of the vein so there is no interference with fluid flowing into the vein through the needle or from the vein through the needle.

U.S. Pat. No. 3,064,648 discloses an intravenous needle assembly in which there are foldable wings on either side of the needle, the foldable wings being defined by weakened portions adjacent to and parallel with the hollow needle. The present invention utilizes similarly formed foldable wings, but more importantly provides the tapered foam pad or its equivalent for positioning the needle at an angle with respect to the vein in which it is positioned.

U.S. Pat. No. 3,863,631 discloses a hollow needle in a combination bandage and mounting device which includes a substantial number of foldable sections which can be used as handles in applying the needle and as bandages and means holding the bandages and the needle in position on the patient's skin.

The present invention has no comparable needle supporting or holding or positioning structure.

U.S. Pat. No. 4,324,236 positions a hollow needle through a hub located between upper and lower lateral wings which extend from the hub, the upper wings providing a hand hold when moved adjacent one another and the lower wings being provided with adhesive surfaces for engagement with the patient's skin. The present invention differs in that a single pair of foldable wings are employed and provides the tapered foam pad or the like for tilting the needle relative to the patient's surface to advantageously position the open beveled end of the needle in the patient's vein.

U.S. Pat. No. 4,392,856 discloses a hollow needle, oppositely disposed wings with a channel therebetween and a cylindrical holder for the needle mounted in a clip in the longitudinal channel. No similar construction is found in the present invention which provides a simple, inexpensive intravenous needle assembly which may be quickly and easily inserted in a patient's vein and adhesively attached to the patient's skin to automatically incline the needle relative to the patient's skin and vein so as to advantageously position the needle in the vein.

SUMMARY OF THE INVENTION

An intravenous needle assembly provides an elongated hollow needle with a beveled end forming a point mounted transversely of a flexible member having oppositely disposed outwardly extending foldable wings, the lower portions of which are provided with a tapered foam pad and an adhesive surface. Flexible connecting tubing engages the needle and extends to a connector. The tapered foam pad or its equivalent yieldable plastic structure automatically positions the needle in inclined relation to the patient's skin and the vein in which the needle is inserted to insure the positioning of the beveled open end of the needle in unencumbered relation to the walls of the vein.

DESCRIPTION OF THE PREFERRED EMBODIMENT

Figure 1:
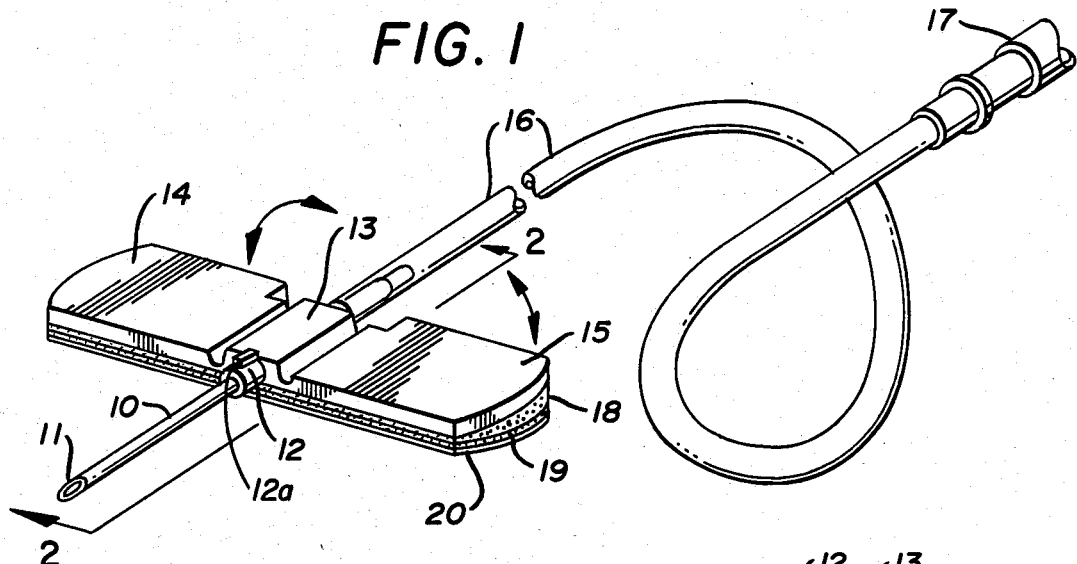
FIG. 1 is an enlarged perspective view of the intravenous needle assembly.
Figure 2:
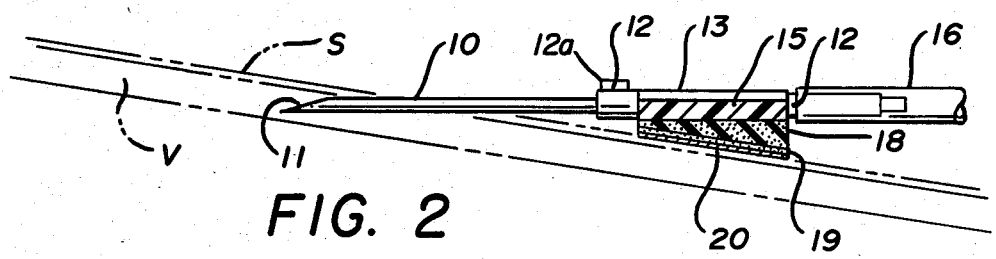
FIG. 2 is a cross section on line 2—2 of FIG. 1, broken lines indicating a skin surface and a vein outline in which the needle is position.
Figure 3:
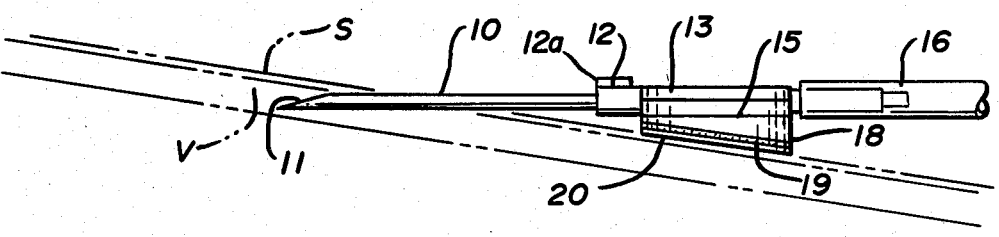
FIG. 3 is a side view of the needle assembly of FIG. 1, broken lines indicating a skin surface and a vein outline in which the needle is inserted.

By referring to the drawings and FIGS. 1, 2 and 3 in particular, it will be seen that the intravenous needle assembly comprises a hollow needle 10 having a pointed end formed by a bevel 11. The hollow needle 10 is positioned in a cylindrical member 12 location transversely of a central body 13 having oppositely disposed outwardly extending wing sections 14 and 15 joined thereto. The central body 13 and the outwardly extending wing sections 14 and 15 are formed of flexible, distortable synthetic resin material so that the wing sections 14 and 15 may be grasped and moved upwardly toward one another where they will form a convenient handle for holding the needle 10 and inserting it in a patient's vein. The opposite end of the needle 10 with respect to the beveled point 11 extends outwardly of the central body 13 and preferably through an extension of the cylindrical member 12 and is secured in one end of a flexible connecting tube 16, the other end of which is provided with a connector 17 by means of which the intravenous needle assembly can be connected to an intravenous body, syringe or the like. A tab 12A is formed on the cylindrical member 12.

Still referring to FIGS. 1, 2 and 3 of the drawings, it will be seen that a tapered pad 18 preferably formed of plastic foam or the like and tapered from one longitudinal edge to the other with its thinnest edge adjacent the side of the central body 13 and outwardly extending wings 14 and 15 from which the pointed end 11 of the hollow needle 10 extends and its thickest edge lying adjacent the opposite side of the central body 13 and the outwardly extending flexible wings 14 and 15 which is adjacent the flexible connecting tube 16.

A layer 19 of pressure sensitive adhesive is positioned on the entire lower surface of the tapered pad 18 and is provided with a removable cover sheet 20.

Still referring to FIGS. 1, 2 and 3 of the drawings, it will be seen that when the cover sheet 20 is removed from the adhesive 19, the oppositely disposed flexible wing sections 14 and 15 may be bent upwardly toward one another to form a convenient handle which may be grasped between the fingers of the physician or nurse positioning the needle assembly in a patient's vein and that upon the needle being positioned in the vein, the flexible wing sections upon being released will assume their normal oppositely disposed position due to the resiliency of the material of which they are formed whereupon they may be moved downwardly into contact with the skin of the patient to secure the intravenous needle assembly in desirable position and still referring to FIGS. 2 and 3 of the drawings, broken lines S and V will be seen to represent a patient's skin and vein in which the intravenous needle assembly has been positioned and it will be observed that the tapered pad 18 has positioned the hollow needle 10 at an angle of about 10 degrees from the plane of the skin surface S and the vein V so that the beveled point 11 is positioned in the vein in spaced relation to the walls of the vein and is therefore unencumbered and permits ready flow of fluid into the vein or blood from the vein as desired.

Figure 4:
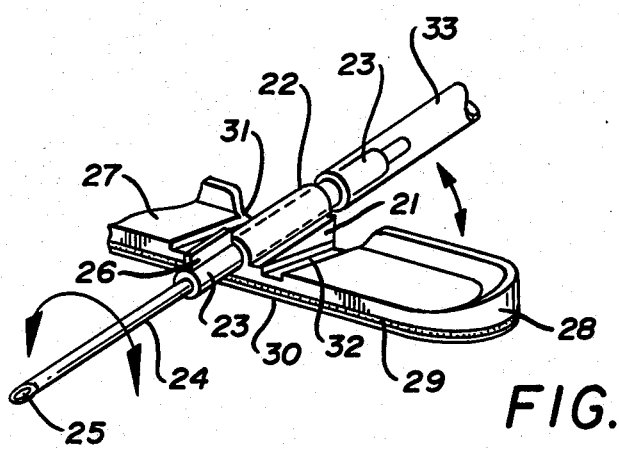
FIG. 4 is a perspective view with parts broken away illustrating a modification in which the needle is rotatable on its longitudinal axis.

A modification of the above-described invention appears in FIG. 4 of the drawings wherein the perspective figure of the modification is partially broken away. The modified intravenous needle assembly comprises an elongated flexible molded plastic body member 21 with a tubular portion 22 transversely thereof and midway between its ends. A sheath 23 is positioned in said tubular portion 22 and carries an elongated hollow needle 24 which is beveled at its pointed end 25. A tab 26 is formed on the sheath 23 so that the sheath 23 and the needle 24 can be rotated on their longitudinal axis by movement imparted the tab 26. The opposite outer portions of the elongated flexible molded plastic body member 21 form wing sections 27 and 28, the lower surfaces of which are positioned on about a 10 degree angle with respect to the longitudinal axis of the sheath 23 and hollow needle 24.

A pressure sensitive adhesive surface 29 is formed on the lower surface of the body member 21 and the wing sections 27 and 28 and it is covered with the usual removable cover sheet 30. Transverse grooves 31 and 32 respectively are formed in the elongated flexible molded plastic body member transversely thereof and alongside the central portion thereof which carries the tubular portion 22. The structure enables the wing sections 27 and 28 to be bent upwardly to locations adjacent one another where they form a convenient handle for the intravenous needle assembly when it is being placed in a patient's vein.

It will be observed that the transversely angular shape of the elongated flexible molded plastic body member 21 including the tubular portion 22 result in the automatically positioning the hollow needle 24 in the patient's vein at an angle with respect to the surface of the skin of the patient to which the elongated flexible molded plastic body member 21 and the wing sections 27 and 28 are adhered when the needle is positioned.

At such time, the tab 26 like the tab 12A in FIG. 1 may be moved through any part or all of a circle to revolve the hollow needle 24 on its longitudinal axis and present the beveled pointed end 25 at a different angle in the patient's vein as may be desirable to insure an unobstructed passageway.

Still referring to FIG. 4 of the drawings, it will be seen that a section of flexible connecting tubing 33 is attached to the tubular sheath 23 on the opposite side of the device with respect to the tab 26. The tubing 33 to be provided with a connection fitting, as known in the art.

It will thus be seen that an intravenous needle assembly has been disclosed which is inexpensive to manufacture, easy to use and automatically positions the needle at an angle to the surface of the patient's skin and the vein thereinunder in which the needle is positioned.

Having thus described my invention, what I claim is:

1. An improvement in an intravenous needle assembly having an elongated flexible body member with a central section and oppositely extending sections wih respect thereto and a hollow needle having a beveled end positioned through said central section transversely of said elongated flexible body member on a transverse horizontal plane; the improvement comprising first means for tilting said elongated flexible body member, and the hollow needle from said transverse horizontal plane to an angular transverse plane with respect to said transverse horizontal plane when said assembly is applied to a patient's skin, and secondary means for rotating said hollow needle on its longitudinal axis, said first means comprising at least one longitudinally extending transversely tapered resilient pad positioned on said elongated flexible body member in oppositely disposed relation to said central section and said hollow needle and said secondary means comprising a cylindrical member rotatably located in said central section and transversely of said elongated flexible body member, said hollow needle positioned in said cylindrical member on said transverse horizontal plane whereby positioning said hollow needle of said assembly through a patient's skin and into a vein of said patient and engaging said tapered pad on said patient's skin tilts said central section and said hollow needle relative to said patient's skin and vein and spaces the beveled end of said hollow needle in unencumbered relation to the walls of said vein.

2. The improvement in an intravenous needle assembly set forth in claim 1 and wherein said oppositely extending sections are thin distortable members positioned on said transverse horizontal plane.

3. The improvement in an intravenous needle assembly set forth in claim 1 and wherein said angular transverse plane is located at about 10° from said transverse horizontal plane.

4. The improvement in an intravenous needle assembly set forth in claims 2, 1 or 3 wherein pressure sensitive adhesive is located on said longitudinally extending transversely tapered pad for holding said assembly in engagement with a patient's skin whereby said central section and said elongated flexible body member and said hollow needle are secured in angular relation to said patient's skin and said vein.

* * * * *